(12) United States Patent
Ranade et al.

(10) Patent No.: US 8,900,619 B2
(45) Date of Patent: Dec. 2, 2014

(54) MEDICAL DEVICES FOR THE RELEASE OF THERAPEUTIC AGENTS

(75) Inventors: Shrirang V. Ranade, Arlington, MA (US); Courtney Sikes, Uxbridge, MA (US); Mark Steckel, Sharon, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1044 days.

(21) Appl. No.: 11/827,462

(22) Filed: Jul. 11, 2007

(65) Prior Publication Data

US 2008/0050418 A1 Feb. 28, 2008

Related U.S. Application Data

(60) Provisional application No. 60/839,750, filed on Aug. 24, 2006.

(51) Int. Cl.
| | | |
|---|---|---|
| A61F 2/00 | (2006.01) | |
| A61L 27/54 | (2006.01) | |
| A61L 31/16 | (2006.01) | |
| A61L 29/14 | (2006.01) | |
| A61L 27/58 | (2006.01) | |
| A61L 29/08 | (2006.01) | |
| A61L 31/14 | (2006.01) | |
| A61L 27/34 | (2006.01) | |
| A61L 31/10 | (2006.01) | |
| A61L 29/16 | (2006.01) | |

(52) U.S. Cl.
CPC ............... *A61L 27/58* (2013.01); *A61L 27/54* (2013.01); *A61L 31/16* (2013.01); *A61L 29/148* (2013.01); *A61L 29/085* (2013.01); *A61L 31/148* (2013.01); *A61L 2300/604* (2013.01); *A61L 27/34* (2013.01); *A61L 31/10* (2013.01); *A61L 29/16* (2013.01)
USPC .......................................... 424/426

(58) Field of Classification Search
None
See application file for complete search history.

(56) References Cited

U.S. PATENT DOCUMENTS

| | | | | |
|---|---|---|---|---|
| 5,527,337 A * | 6/1996 | Stack et al. | ............ | 606/198 |
| 5,733,925 A | 3/1998 | Kunz et al. | ............ | 514/449 |
| 6,517,889 B1 * | 2/2003 | Jayaraman | ............ | 427/2.24 |
| 6,545,097 B2 | 4/2003 | Pinchuk et al. | ............ | 525/240 |
| 2002/0006443 A1 | 1/2002 | Curatolo et al. | ............ | 424/486 |
| 2003/0153971 A1 | 8/2003 | Chandrasekaran | ............ | 623/1.15 |
| 2003/0153972 A1 | 8/2003 | Helmus | ............ | 623/1.15 |
| 2003/0236514 A1 | 12/2003 | Schwarz | ............ | 604/890.1 |
| 2004/0053894 A1 * | 3/2004 | Mazess et al. | ............ | 514/167 |
| 2004/0106987 A1 * | 6/2004 | Palasis et al. | ............ | 623/1.42 |
| 2005/0112170 A1 | 5/2005 | Hossainy et al. | | |
| 2005/0147647 A1 * | 7/2005 | Glauser et al. | ............ | 424/426 |
| 2005/0186276 A1 | 8/2005 | Berchielli et al. | ............ | 424/468 |
| 2005/0208093 A1 * | 9/2005 | Glauser et al. | ............ | 424/423 |
| 2006/0051390 A1 | 3/2006 | Schwarz | ............ | 424/422 |
| 2006/0147491 A1 * | 7/2006 | DeWitt et al. | ............ | 424/426 |
| 2006/0161242 A1 * | 7/2006 | Lee et al. | ............ | 623/1.15 |
| 2006/0217798 A1 * | 9/2006 | Santini et al. | ............ | 623/1.42 |
| 2006/0229711 A1 * | 10/2006 | Yan et al. | ............ | 623/1.38 |
| 2007/0178135 A1 | 8/2007 | Zhong | ............ | 424/426 |

FOREIGN PATENT DOCUMENTS

| | | | | |
|---|---|---|---|---|
| EP | 1362603 A2 | 11/2003 | | |
| WO | 0224247 A1 | 3/2002 | | |
| WO | WO 2005/038465 | * | 4/2005 | ............ G01N 33/74 |
| WO | 2005113034 A1 | 12/2005 | | |
| WO | 2007126606 A2 | 11/2007 | | |

OTHER PUBLICATIONS

Cottrell et al. (Sorbitan esters and polysorbates, Emulsifiers in Food Technology, 2004.*
Lu et al., "In vitro degradation of porous poly(L-lactic acid) foams," *Biomaterials*, 21 (2000):1595-1605.
K. Rezwan et al., "Biodegradable and bioactive porous polymer/inorganic composite scaffolds for bone tissue engineering," *Biomaterials*, vol. 27, (2006) pp. 3413-3431.
F. Aulenta et al., "Dendrimers: a new class of nanoscopic containers and delivery devices", *European Polymer Journal*, vol. 39 (2003) pp. 1741-1771.
M. Liu et al., "Designing dendrimers for durg delivery", *PSTT*, vol. 2, No. 10, Oct. 1999, pp. 339-401.

* cited by examiner

*Primary Examiner* — Dennis Heyer
*Assistant Examiner* — Daniel M Podgorski
(74) *Attorney, Agent, or Firm* — Fish & Richardson P.C.

(57) ABSTRACT

According to one aspect of the invention, medical devices are provided which contain the following: (a) an interior region that contains at least one degradation promoting agent and (b) an exterior region disposed over the interior region that contains at least one biodegradable polymer and at least one therapeutic agent.

37 Claims, 3 Drawing Sheets

MEDICAL DEVICES FOR THE RELEASE OF THERAPEUTIC AGENTS

STATEMENT OF RELATED APPLICATION

This application claims the benefit of U.S. Provisional Patent Application Ser. No. 60/839,750, filed Aug. 24, 2006, entitled "Medical Devices for the Release of Therapeutic Agents", which is incorporated by reference herein.

FIELD OF THE INVENTION

The present invention relates to medical devices which are a least partially biodegradable and which release therapeutic agents.

BACKGROUND

Numerous polymer-based medical devices have been developed for implantation or insertion into the body. For example, in recent years, drug eluting coronary stents, which are commercially available from Boston Scientific Corp. (TAXUS), Johnson & Johnson (CYPHER) and others, have become the standard of care for maintaining vessel patency. These existing products are based on metallic balloon expandable stents with biostable polymer coatings, which release antiproliferative drugs at a controlled rate and total dose.

Specific examples of biostable polymers for drug eluting polymer coatings include block copolymers of polyisobutylene and polystyrene, for example, polystyrene-polyisobutylene-polystyrene triblock copolymers (SIBS copolymers), which are described in U.S. Pat. No. 6,545,097 to Pinchuk et al., which have proven valuable in implantable and insertable medical devices for a variety of reasons, including their excellent elasticity, strength and biocompatibility. SIBS copolymer systems are also effective drug delivery systems for providing therapeutic agents to sites in vivo.

Biodegradable polymers, on the other hand, offer the potential of reducing or eliminating long term effects that may be associated with non-biodegradable polymers (e.g., foreign body effects, etc.), because they are metabolized over time.

SUMMARY OF THE INVENTION

According to an aspect of the invention, medical devices are provided which comprise the following: (a) an interior region that comprises at least one degradation promoting agent and (b) an exterior region disposed over the interior region that comprises at least one biodegradable polymer and at least one therapeutic agent.

Other aspects, as well as various embodiments and advantages of the present invention will become immediately apparent to those of ordinary skill in the art upon reading the disclosure to follow.

DETAILED DESCRIPTION OF THE INVENTION

Figure 1:
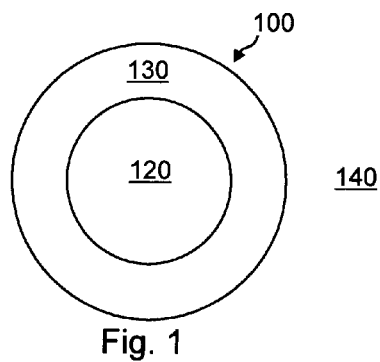
FIG. 1 is a schematic view of a medical device or portion thereof that is substantially circular in cross-section, in accordance with an embodiment of the invention.

According to one aspect of the present invention, medical devices are provided which comprise the following: (a) an interior region that comprises at least one degradation promoting agent and (b) an exterior region disposed over the interior region that comprises at least one biodegradable polymer and at least one therapeutic agent. As a consequence of this arrangement, the exterior region is situated between the interior region and an exterior environment surrounding the medical device. Thus, the exterior region is positioned to regulate transport of chemical species between the exterior environment and the interior region. As used herein a polymer is biodegradable if it undergoes bond cleavage along the polymer backbone in vivo, regardless of the mechanism of bond cleavage (e.g., enzymatic breakdown, hydrolysis, oxidation, etc.)

By "exterior" is meant that the region is exterior relative to the interior region—not that it is necessarily the most exterior region of the device (for example, the exterior region may in turn be covered by another more-exteriorly-positioned region such as an outer biodegradable hydrogel layer, etc.). Similarly, by "interior" is merely meant that the region is interior relative to the exterior region—not that it is necessarily the most interior region of the device.

In certain embodiments of the invention, the exterior region may contain, for example, (a) from 50 wt % or less to 75 wt % to 90 wt % to 95 wt % to 97.5 wt % to 99 wt % or more of at least one biodegradable polymer and (b) from 1 wt % or less to 2.5 wt % to 5 wt % to 10 wt % to 25 wt % to 50 wt % or more of at least one therapeutic agent.

In certain embodiments, the interior region may further contain a biodisintegrable material (i.e., a material that disintegrates in vivo due to one or more mechanisms such as dissolution, degradation, resorption, etc.) in addition to the degradation promoting agent. In such embodiments, the interior region may comprise, for example, (a) from 1 wt % or less to 2.5 wt % to 5 wt % to 10 wt % to 25 wt % to 50 wt % or more of at least one degradation promoting agent and (b) from 50 wt % or less to 75 wt % to 90 wt % to 95 wt % to 97.5 wt % to 99 wt % or more of at least one biodisintegrable material. In certain embodiments, the biodisintegrable material in the interior region is a biodegradable polymer, which may be the same as or different from the biodegradable polymer in the exterior region.

Typically, both the interior and exterior regions are adapted to be substantially completely biodisintegrated (i.e., 95 wt % to 97.5 wt % to 99 wt % or more wt % of each region disintegrates in vivo due to one or more mechanisms such as dissolution, degradation, resorption, etc.) over the period that the device is designed to reside in a patient.

As is well known, "polymers" are molecules containing multiple copies (e.g., 5 to 10 to 25 to 50 to 100 to 250 to 500 to 1000 or more copies) of one or more constitutional units, commonly referred to as monomers. Polymers may take on a number of configurations, which may be selected, for example, from cyclic, linear, branched and networked (e.g., crosslinked) configurations. Branched configurations include star-shaped configurations (e.g., configurations in which three or more chains emanate from a single branch point, such as a seed molecule), comb configurations (e.g., configurations having a main chain and a plurality of side chains), dendritic configurations (e.g., arborescent and hyperbranched polymers), and so forth. As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating), and block copolymers.

Examples of biodegradable polymers for use in the present invention may be selected from suitable members of the following, among many others: (a) polyester homopolymers and copolymers such as polyglycolide, poly-L-lactide, poly-D-lactide, poly-D,L-lactide, poly(beta-hydroxybutyrate), poly-D-gluconate, poly-L-gluconate, poly-D,L-gluconate, poly(epsilon-caprolactone), poly(delta-valerolactone), poly(p-dioxanone), poly(trimethylene carbonate), poly(lactide-co-glycolide) (PLGA), poly(lactide-co-delta-valerolactone), poly(lactide-co-epsilon-caprolactone), poly(lactide-co-beta-malic acid), poly(lactide-co-trimethylene carbonate), poly(glycolide-co-trimethylene carbonate), poly(beta-hydroxybutyrate-co-beta-hydroxyvalerate), poly[1,3-bis(p-carboxyphenoxy)propane-co-sebacic acid], and poly(sebacic acid-co-fumaric acid), among others, (b) poly(ortho esters) such as those synthesized by copolymerization of various diketene acetals and diols, among others, (c) polyanhydrides such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride] and poly[1,3-bis(p-carboxyphenoxy)hexane anhydride], among others; and (d) amino-acid-based polymers including tyrosine-based polyarylates (e.g., copolymers of a diphenol and a diacid linked by ester bonds, with diphenols selected, for instance, from ethyl, butyl, hexyl, octyl and bezyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and bezyl esters of desaminotyrosyl-tyrosine), and tyrosine-, leucine- and lysine-based polyester-amides; specific examples of tyrosine-based polymers include includes polymers that are comprised of a combination of desaminotyrosyl tyrosine hexyl ester, desaminotyrosyl tyrosine, and various di-acids, for example, succinic acid and adipic acid, among others.

Examples of medical devices benefiting from the present invention include implantable or insertable medical devices, for example, catheters (e.g., urological or vascular catheters such as balloon catheters and various central venous catheters), guide wires, balloons, filters (e.g., vena cava filters and mesh filters for distil protection devices), stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, embolization devices including cerebral aneurysm filler coils (including Guglilmi detachable coils and metal coils), embolic agents, hermetic sealants, septal defect closure devices, myocardial plugs, patches, pacemakers, lead coatings including coatings for pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, as well as various other devices that are implanted or inserted into the body and from which therapeutic agent is released.

The medical devices of the present invention thus include, for example, implantable and insertable medical devices that are used for systemic treatment, as well as those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth and bone. As used herein, "treatment" refers to the prevention of a disease or condition, the reduction or elimination of symptoms associated with a disease or condition, or the substantial or complete elimination of a disease or condition. Preferred subjects are vertebrate subjects, more preferably mammalian subjects and more preferably human subjects.

In some embodiments, the above-described interior and exterior regions of the present invention, in combination, correspond to an entire medical device. In other embodiments, these regions correspond to one or more portions of a medical device. For instance, the interior and exterior regions can be in the form of one or more medical device components, in the form of one or more fibers which are incorporated into a medical device, in the form of layers formed over all or only a portion of an underlying medical device substrate, and so forth. Layers can be provided over an underlying substrate region at a variety of locations, and in a variety of shapes (e.g., in desired patterns, for instance, using appropriate application or masking techniques). As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

In an aspect of the invention, at least one therapeutic agent is delivered into a subject from an exterior region of a medical device, which exterior region comprises the at least one therapeutic agent and at least one biodegradable polymer. Once the therapeutic agent has been delivered from the exterior region at a suitable rate and for a suitable period of time (i.e., once the exterior region has provided a suitable delivery profile for the application at hand, e.g., prevention of restenosis, etc.), the biodegradable polymer component is no longer needed and, in fact, may actually be undesirable (e.g., due to foreign body effects, etc.).

As a specific example, intraluminal stents are commonly inserted or implanted into body lumens, for instance, into a coronary artery after a procedure such as percutaneous transluminal coronary angioplasty ("PCTA"). Such stents are used to maintain the patency of the coronary artery by supporting the arterial walls and preventing reclosure or collapse thereof, which can occur after PCTA. Metals such as stainless steel or nitinol are commonly used for this purpose as they are strong and have good vascular biocompatibility. These stents can also be provided with one or more therapeutic agents adapted to be locally released from the stent at the site of implantation. In the case of a coronary stent, the stent can be adapted to release, for example, an antithrombotic agent to inhibit clotting or an antiproliferative agent to inhibit re-narrowing or restenosis of the blood vessel after implantation of the stent. Unfortunately, materials such as stainless steel are not particularly desirable as drug delivery reservoirs. Polymers, including various biodegradable polymers (e.g., PLGA), on the other hand, may be readily used for this purpose. However, because such materials are commonly less biocompatible than the underlying metallic stent material, it may be desirable to clear the polymer from the implant site as quickly as possible after the drug delivery role of the polymer has been fulfilled.

One approach is to use a polymer in the coating layer that is inherently rapidly cleared by biodegradation. As a specific example, the biodegradation rate of PLGA may be increased by increasing the amount of glycolide monomer relative to the lactide monomer within the polymer (e.g., by moving from a 75:25 lactide:glycolide ratio to a 50:50 lactide:glycolide ratio, among other possibilities). In some instances, however, increasing the biodegradation rate by varying the biodegradable polymer composition of the coating material can adversely affect other properties of the coating material, including, for instance, the therapeutic-agent delivery profile of the coating material. For example, although increasing the amount of glycolide monomer relative to the lactide monomer within the copolymer will accelerate biodegradation rate of the copolymer, the fact that glycolide monomer is more hydrophilic than lactide monomer also means that the hydrophobic-hydrophilic balance of the polymer is changed. Consequently, the duration of drug delivery may become unacceptably altered by the change in composition (e.g., by becoming unacceptably short). PLGA is by no means unique in this respect. For example, tyrosine-derived ester-amides such as the TyRx 2,2 family of polymers, available from TyRx Pharma, Inc., Monmouth Junction, N.J., USA, also undergo a similar increase in hydrophilicity with increasing biodegradation rate.

An advantage of the present invention, in contrast to the above situation, is that one can maintain a desired polymer property (e.g., drug delivery) for a finite time (e.g., while the drug delivery property is needed and desirable), after which the polymer degradation process is accelerated. This is achieved in the present invention by providing a two-region system in which an exterior region is provided, which contains a drug and a biodegradable polymer (which, for example, acts as a matrix from the drug), and an interior region is provided, which contains a polymer degradation promoting agent.

For example, various biodegradable polymer regions, including biodegradable materials containing various polyesters, are known to degrade via hydrolysis. Moreover, water is known to diffuse, over the course of days to weeks, from the surface of such polymer regions and into bulk, with the time required depending, for example, on the thickness of the biodegradable polymer region, on the crystallinity and hydrophobicity of the polymer(s) within the region, and on the concentration and hydrophobicity of any agents (e.g., drugs, etc.) within the region, among other factors. Where an exterior region in accordance with the present invention contains such polymers, the exterior region thus initially degrades at a rate that is defined by these factors, which are based on the dimensions of the exterior region and the materials forming the same. At the same time, the exterior region provides a drug release profile that is also based on the dimensions of the exterior region and the materials forming the same. However, once the water penetrates to a depth where it interacts with the degradation promoting agent in the interior region, the polymer degradation rate increases. For example, the degradation promoting agent may affect the degradation rate of the exterior region by diffusing into the now-hydrated exterior region and interacting with the biodegradable polymer in that region. (Note that if the degradation promoting agent were simply admixed with the biodegradable polymer and therapeutic agent in the exterior region, control over drug elution could be lost.) The degradation promoting agent may also affect the degradation rate of the exterior region by first causing increased (relative to the exterior region) biodegradable polymer breakdown in the interior region, followed by diffusion of degradation products into the exterior region. In this regard, breakdown products of various biodegradable polymers, including various biodegradable polyesters, are known to be autocatalytic, thereby promoting further polymer breakdown.

As noted above, polyesters and various other biodegradable polymers are known to dissolve via hydrolysis. Hydrolysis may be increased, for example, by promoting transport of reactants (e.g., water) into the polymer region where the reactants can participate in the hydrolysis reaction. Hydrolysis may also be increased, for example, by promoting transport of reaction products (e.g., polymer breakdown products such as monomers and multimers) away from the reaction site in the polymer bulk. For this purpose, particles of poragenic agents can be supplied as degradation promoting agents within the interior region. These are materials which can readily disintegrate (e.g., based on dissolution, rapid biodegradation, etc.) and form pores in the interior region, thereby increasing transport of water into, and transport of reaction products out of, the interior region. As noted above, certain reaction products are autocatalytic, causing further polymer breakdown.

As another example, solubilizing agents can be provided as degradation promoting agents within the interior region. For instance, these agents can increase the solubility of the polymer breakdown reaction products, thereby assisting in the removal of reaction products from the device. Note that the solubilizing agents may assist in the removal of reaction products from the interior region, the exterior region (e.g., by diffusing from the interior region and into the exterior region), or both.

Biodegradation may also be increased, for example, by the addition of degradation promoting agents that that act to catalyze (i.e., speed up) the rate of biodegradation. Examples catalytic species include enzymes and acidic species. With respect to the latter, it is known that polyester hydrolysis is acid catalyzed. In this respect, polyester hydrolysis has been reported to be autocatalytic in that acidic species are produced during hydrolysis (e.g., hydroxyacids, etc.), which accelerate further hydrolysis. The catalytic agents may promote hydrolysis within the interior region, the exterior region (e.g., by diffusing from the interior region and into the exterior region), or both.

Note that the above categories of degradation promoting agents are not necessarily mutually exclusive. For example, solubilizing agents may act as poragenic agents and vice versa, catalytic agents may act as poragenic agents and vice versa, and so forth. Note also that these agents can be used in combination.

Suitable poragenic agents for use as degradation promoting agents may be selected, for example, from (a) readily disintegrable therapeutic agents such as aspirin and lactose, among many others, (b) proteins and peptides including gelatin, collagen, albumin, and tyrosinase, among may others, (c) salts including potassium chloride, sodium chloride and calcium chloride, among may others, (d) monosaccharides and polysaccharides, including di-, tri-, tetra-, penta-, etc. saccharides, for example, sugars including galactose, glucose and sucrose and polysaccharides including soluble celluloses, glycosaminoglycans and proteoglycans such as heparin, heparin sulfate, hyaluronic acid and its salts, dermatan sulfate, keratin sulfate, and chrondroitin sulfate, starch, dextran, dextran derivatives, chitosan, alginic acid and its various salts, cyclodextrins and blends of the same, among may others, (e) soluble and rapidly biodegradable polymers such as polyanhydrides and polyorthoesters, among may others, and (e) mixtures of the same.

Examples of solubilizing agents for use as degradation promoting agents include compounds that increase the solubility of biodegradation reaction products by intimately associating with the same, for instance, based on one or more of the following non-covalent interactions, among others: electrostatic interactions (e.g., ion-ion, ion-dipole, dipole-dipole), hydrogen bonding interactions, π-π stacking interactions, cation-π interactions, Van der Waals interactions, and hydrophobic effects. These agents may spontaneously associate with the reaction products (e.g., by forming host-guest or other complexes, by self-assembling into micelles, by self-emulsifying, or by spontaneously forming other associations with the reaction products).

Specific examples of solubilizing agents include suitable members of the following: (a) host molecules and their derivatives which have internal cavities (including notches, etc.) of molecular dimensions and which may act as hosts for hydrophobic guest molecules, for example, those host molecules having relatively hydrophobic cavities and relatively hydrophilic exteriors, such as macro(poly)cyclic compounds including calixarenes, cyclodextrins (e.g., alpha-, beta-, gamma-, delta-, etc. cyclodextrins, and their derivatives, including cationic derivatives and derivatives with hydroxypropyl and sulfobutyl ether groups, among others), crown ethers (and their derivatives), and so forth; (b) dendrimers, including those that form so-called "unimolecular micelles" in water, which typically have a relatively hydrophobic interior and a relatively hydrophilic chain ends, for example, those having interiors selected from poly(aryl ether), poly (amidoamine) (PAMAM), poly(1,4-diaminobutane) (DAB), and poly(propylene imine) and those terminated with hydrophilic end groups or hydrophilic end chains selected from ionic end groups such as carboxylate end groups, poly(ionic monomer) end chains such as polyacrylic acid end chains, poly(hydrophilic monomer) end chains, for instance, polyethylene oxide or polypropylene oxide chains, such as those having from 2 to 4 to 8 to 12 to 20 monomers or more, and so forth; (c) various ionic (e.g., cationic, anionic, zwitterionic) and non-ionic surfactants; mono-, di-, and tri-glycerides (e.g., glycerol monostearate, glycerol distearate, glycerol monolaurate, etc.); polyhydric alcohol esters; phospholipids, such as lecithin; partial (e.g., mono-, di-, tri-, etc.) fatty acid esters of sugars and sugar alcohols such as sucrose (e.g. sucrose monolaurate and sucrose monostearate, among other sucrose fatty acid esters) and sorbitol (e.g., sorbitan monolaurate, sorbitan monostearate, sorbitan monooleate, sorbitan monopalmitate, sorbitan sesquioleate, sorbitan trioleate, sorbitan tristearate, sorbitan monododecanoate, sorbitan monohexadecanoate, sorbitan monooctadecanoate, sorbitan trioctadecanoate, sorbitan mono-9-monodecenoate, and sorbitan tri-9-octadecenoate, among other sorbitan fatty acid esters); fatty alcohol ethers of oligoglucosides (e.g., akylpolyglucosides); polyoxyalkylenes such as polyoxyethylene and polyoxypropylene as well as their derivatives and copolymers (note that polyoxyethylene, polyoxyethylene ether, polyethylene glycol and polyethylene oxide are often used synonymously in the art), for example, polyoxyethylene-polyoxypropylene block copolymers (also known as poloxamers, e.g., those sold by BASF as Pluronic® surfactants) and polyoxyalkylene derivatives such as polyoxyalkylene esters, including polyethylene glycol esters, polypropylene glycol esters, polyoxyalkylene sorbitan esters such as polyethoxylated fatty acid esters of sorbitan (e.g., polysorbates), and fatty acid esters of polyethylene oxide (e.g., polyoxyethylene stearates), polyoxyalkylene ethers, including fatty alcohol ethers of polyethylene oxide (e.g., polyoxyethylated lauryl ether) and alkylphenol ethers of polyethylene oxide (e.g., polyethoxylated octylphenol), and ethoxylated fats and oils (e.g., ethoxylated castor oil and polyoxyethylated castor oil, also known as polyethylene glycol-glyceryl triricinoleate, and so forth; and (d) mixtures of the foregoing. For further examples of solubilizing agents, see, e.g., U.S. Patent Appln. Nos. 2005/0186276 to Berchielli et al., 2004/0053894 to Mazess et al., and 2002/0006443 to Curatolo et al. see also F. Aulenta et al., "Dendrimers: a new class of nanoscopic containers and delivery devices," European Polymer Journal 39 (2003) 1741-1771; and M. Liu and J. M. M. Frechet; "Designing dendrimers for drug delivery," PSTT Vol. 2, No. 10 (October 1999) 393-401.

Suitable catalytic agents for use as degradation promoting agents may be selected, for example, from (a) enzymes such as tyrosinase and lipase, among others, and (b) acidic species, for example, organic and inorganic acids, such as ascorbic, benzoic, edetic, sebacic, sorbic, glutamic, p-toluenesulfonic, citric, succinic, fumaric, adipic, malic, tartaric, lactic, and glycolic acids, among others.

As noted above, the external regions of the medical devices of the present invention contain one or more therapeutic agents. "Therapeutic agents," "drugs," "pharmaceutically active agents," "pharmaceutically active materials," and other related terms may be used interchangeably herein. These terms include genetic therapeutic agents, non-genetic therapeutic agents and cells.

Exemplary non-genetic therapeutic agents for use in conjunction with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Specific examples of non-genetic therapeutic agents include paclitaxel, (including particulate forms thereof, for instance, protein-bound paclitaxel particles such as albumin-bound paclitaxel nanoparticles, e.g., ABRAXANE), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Exemplary genetic therapeutic agents for use in conjunction with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in conjunction with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK (D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin (sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Further additional therapeutic agents useful for the practice of the present invention are also disclosed in U.S. Pat. No. 5,733,925 assigned to NeoRx Corporation, the entire disclosure of which is incorporated by reference.

As previously noted, in some embodiments, the interior and exterior regions of the medical devices of the present invention may collectively correspond to an entire medical device. In other embodiments, the interior and exterior regions may correspond or to one or more portions of a medical device. In some of these embodiments, for example, the interior and exterior regions may be in the form of layers formed over all or only a portion of an underlying medical device substrate. Materials for use as underlying substrate regions include polymeric materials, ceramic materials and metallic materials.

Examples of some possible configurations for the various regions of the invention (e.g., exterior, interior and optional substrate regions) will now be described in conjunction with the drawings.

FIG. 1, for example, is a schematic view of a medical device or portion thereof 100 that is substantially cylindrical in cross-section (e.g., a fiber, rod, screw, etc.). The device or portion thereof 100 comprises an interior region 120 and an exterior region 130. As previously noted, the exterior region 130 is disposed between the exterior environment 140 surrounding the medical device and the interior region 120. Thus, the exterior region 130 is positioned to regulate transport of chemical species between the exterior environment 140 and the interior region 120.

Figure 2:
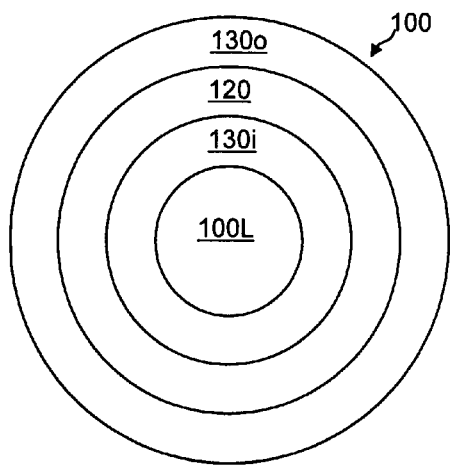
FIG. 2 is a schematic view of a medical device or portion thereof that is substantially annular in cross-section, in accordance with an embodiment of the invention.

Another specific embodiment will now be described with reference to FIG. 2, which is a schematic view of a medical device or portion thereof 100 that is substantially annular in cross-section (e.g. a tube, stent, etc.). The medical device or portion thereof 100 has an inner lumen 100L, and comprises (a) an annular interior region 120, (b) an exterior region 130i disposed on an inner surface of the annular interior region 120 (e.g., in the form of an inner coating layer) and (c) an exterior region 130o disposed on an outer surface of the annular interior region 120 (e.g., in the form of an outer coating layer).

Figure 3:
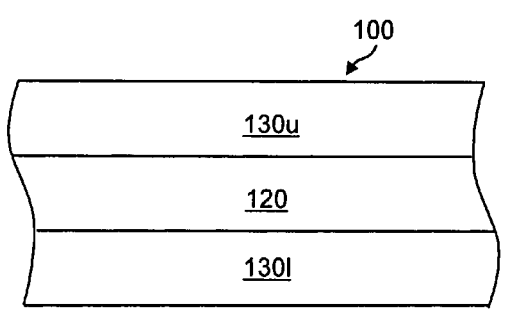
FIG. 3 is a schematic partial cross-sectional view of a substantially planar medical device or portion thereof, in accordance with an embodiment of the invention.

Yet another specific embodiment is shown in FIG. 3, which is a partial schematic cross-sectional view of a substantially planar medical device or portion thereof 100 (e.g., a patch, tissue engineering scaffold, etc.). The medical device or portion thereof 100 comprises (a) a substantially planar interior region 120, (b) an exterior region 130l disposed on a lower surface of the interior region 120 (e.g., in the form of a lower coating layer) and (c) an exterior region 130u disposed on an upper surface of the interior region 120 (e.g., in the form of an upper coating layer).

Figure 4:
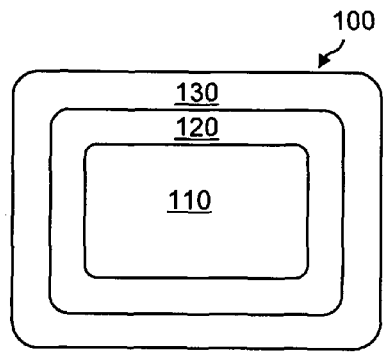
FIG. 4 is a schematic view of a medical device or portion thereof that is substantially rectangular in cross-section, in accordance with an embodiment of the invention.
Figure 8:
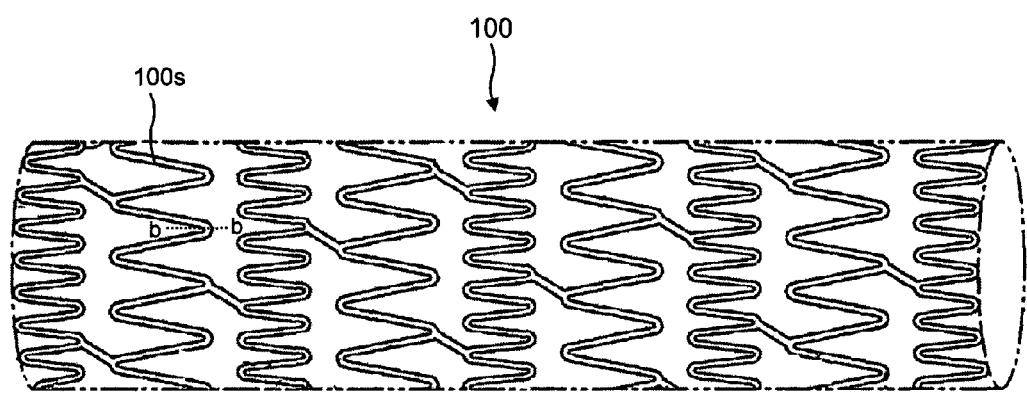
FIG. 8 is a schematic perspective view of a coronary stent, in accordance with an embodiment of the invention.

As noted above, in various aspects of the invention, inner and outer regions are associated with a substrate region. One specific embodiment of this aspect of the invention is shown in FIG. 4, which is a schematic view of a medical device or portion thereof 100 that is substantially rectangular in cross-section. (FIG. 4 may correspond, for example, a cross-section of a stent strut, such as that taken along line b-b of strut 110s of stent 100 of FIG. 8.) The device or portion thereof 100 comprises a substrate region 110, an interior region 120 (e.g., in the form of an inner layer provided over the substrate region 110), and an exterior region 130 (e.g., in the form of an outer layer provided over the inner region 120).

Figure 5:
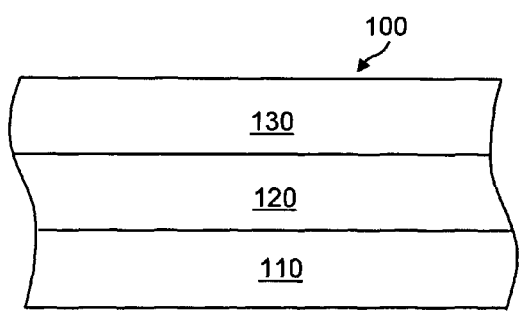
FIG. 5 is a schematic partial cross-sectional view of a substantially planar medical device or portion thereof, in accordance with an embodiment of the invention.

Another specific embodiment will now be described with reference to FIG. 5, which is a partial schematic cross-sectional view of a substantially planar medical device or portion thereof 100. The device or portion thereof 100 comprises a substantially planar substrate region 110, an interior region 120 (e.g., in the form of an inner layer provided over the substrate region 110), and an exterior region 130 (e.g., in the form of an outer layer provided over the inner region 120).

Figure 6:
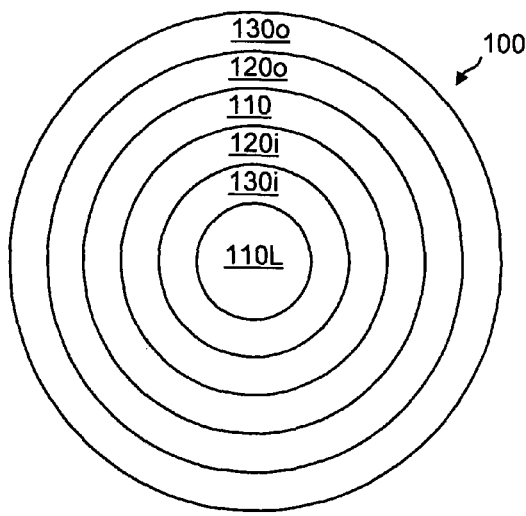
FIG. 6 is a schematic view of a medical device or portion thereof that is substantially annular in cross-section, in accordance with an embodiment of the invention.

Another specific embodiment of the invention is described with reference to FIG. 6, which is a schematic view of a medical device or portion thereof 100 that is substantially annular in cross-section. The device or portion thereof 100 has an inner lumen 100L and comprises an annular substrate region 110, an interior region 120i disposed on an inner surface of the substrate region 110, an interior region 120*o* disposed on an outer surface of the substrate region 110, an exterior region 130*i* disposed on an inner surface of the interior region 120*i*, and an exterior region 130*o* disposed on an outer surface of the interior region 120*o*.

Figure 7:
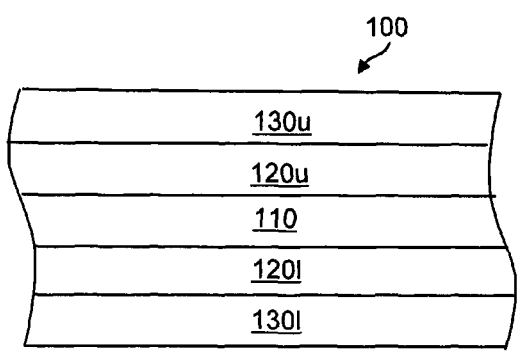
FIG. 7 is a schematic partial cross-sectional view of a substantially planar medical device or portion thereof, in accordance with an embodiment of the invention.

Still another specific embodiment will now be described with reference to FIG. 7, which illustrates a partial cross section of a generally planar medical device or portion thereof 100. The device or portion thereof 100 comprises a substantially planar substrate region 110, an interior region 120*u* disposed on an upper surface of the substrate region 110, an interior region 120*l* disposed on a lower surface of the substrate region 110, an exterior region 130*u* disposed on an upper surface of the interior region 120*u*, and an exterior region 130*l* disposed on a lower surface of the interior region 120*l*.

Obviously, innumerable other configurations are possible for medical devices which comprise an exterior region, an interior region and an optional substrate region.

Numerous techniques are available for forming the various regions of the medical devices (or portions thereof) of the invention.

For example, in some embodiments, solvent-based techniques are used to form one or more of the various regions of the present invention (e.g., the optional substrate region, the interior region, and/or the exterior region). Using these techniques, regions can be formed by first providing a solution that contains the chemical species that make up the regions (e.g., biodegradable polymer, therapeutic agent, degradation promoting agent, and/or other species), dissolved or dispersed therein, and subsequently removing the solvent system. The solvent system that is ultimately selected will contain one or more solvent species, which may be selected based on their ability to dissolve or disperse the various chemical species, as well as other factors, including drying rate, surface tension, etc. Examples of solvent-based techniques include solvent casting techniques, spin coating techniques, web coating techniques, solvent spraying techniques, dipping techniques, techniques involving coating via mechanical suspension including air suspension, ink jet techniques, electrostatic techniques, and combinations of these processes, among others.

In other embodiments, thermoplastic processing techniques are used to form one or more of the various regions of the present invention. Using these techniques, regions can be formed by first providing a melt that contains the chemical species that make up the regions, and subsequently cooling the melt. Examples of thermoplastic techniques include compression molding, injection molding, blow molding, spinning, vacuum forming and calendaring, as well as extrusion into sheets, fibers, rods, tubes and other cross-sectional profiles of various lengths. Using these and other thermoplastic processing techniques, a variety of regions can be formed In some embodiments of the invention, a solution (where solvent-based processing is employed) or melt (where thermoplastic processing is employed) is applied to an underlying region. For example, the underlying region may correspond to all or a portion of an implantable or insertable medical device substrate to which an interior region is first applied and to which an exterior region may subsequently be applied. The underlying region can also be, for example, a template, such as a mold, from which the subsequently applied region may be removed after solidification. In still other embodiments, for example, co-extrusion techniques, two or more regions may be formed without the aid of a substrate. For example, interior and exterior regions may be coextruded together; substrate, interior and exterior regions may be coextruded together; and so forth.

Other ways of forming medical devices in accordance with the present invention will become readily apparent to those of ordinary skill upon review of the above description of the invention.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising: (a) a metallic substrate which is a metal stent body; (b) a biodisintegrable interior region disposed directly on said substrate, that comprises a degradation promoting agent selected from organic acids, polyoxyalkylene homopolymers, polyoxyalkylene copolymers, polyoxyalkylene esters, polyoxyalkylene ethers, or combination thereof, and particulate poragenic agents and does not comprise a biodegradable polymer and (c) a biodisintegrable exterior region, disposed between the interior region and an exterior environment of the device, which comprises a biodegradable polymer and a therapeutic agent.

2. The medical device of claim 1, wherein the degradation promoting agent is a particulate poragenic agent selected from potassium chloride, sodium chloride, calcium chloride, amino acids, and sugars.

3. The medical device of claim 2, wherein said poragenic agent is a sugar.

4. The medical device of claim 1, wherein the degradation promoting agent is a polyoxyalkylene homopolymer, polyoxyalkylene copolymer, polyoxyalkylene ester, polyoxyalkylene ether, or combination thereof.

5. The medical device of claim 4, wherein said degradation promoting agent is a polyoxyalkylene sorbitan ester.

6. The medical device of claim 4, wherein said degradation promoting agent is a polyethoxylated fatty acid ester of sorbitan.

7. The medical device of claim 4, wherein said degradation promoting agent is a polysorbate.

8. The medical device of claim 1, wherein the degradation promoting agent is an organic acid.

9. The medical device of claim 7, wherein said organic acid is citric acid.

10. The medical device of claim 1, wherein the interior region comprises a plurality of differing degradation promoting agents.

11. The medical device of claim 10, wherein the degradation promoting agent comprises a polyoxyalkylene homopolymer, polyoxyalkylene copolymer, polyoxyalkylene ester, polyoxyalkylene ether, or combination thereof and a particulate poragenic agent.

12. The medical device of claim 11, wherein the particulate poragenic agent is selected from potassium chloride, sodium chloride, calcium chloride and a sugar.

13. The medical device of claim 11, wherein the particulate poragenic agent is a sugar.

14. The medical device of claim 1, wherein the biodegradable polymer is a polyester.

15. The medical device of claim 14, wherein the polyester comprises lactide monomers, glycolide monomers, or both.

16. The medical device of claim 1, wherein the biodegradable polymer is an amino-acid-based polymer.

17. The medical device of claim 16, wherein the amino-acid-based polymer is a tyrosine-based polymer.

18. The medical device of claim 1, wherein the exterior region comprises a plurality of differing biodegradable polymers.

19. The medical device of claim 1, wherein said therapeutic agent is selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, agents that interfere with endogenous vasoactive mechanisms, or combinations thereof.

20. The medical device of claim 1, wherein the exterior region comprises a plurality of differing therapeutic agents.

21. The medical device of claim 1, wherein said stent body is stainless steel or nitinol.

22. The medical device of claim 1, wherein the interior region comprises 50 wt % or more of said degradation promoting agent.

23. The medical device of claim 1, wherein said device releases a single therapeutic agent.

24. The medical device of claim 1, wherein said biodisintegrable exterior region is disposed directly on said biodisintegrable interior region.

25. The medical device of claim 24, wherein the degradation promoting agent is a particulate poragenic agent.

26. The medical device of claim 25, wherein said poragenic agent is a sugar.

27. A medical device comprising: (a) a metallic stent substrate which is a metal stent body; (b) a biodisintegrable interior region disposed directly on said substrate that comprises a solubilizing agent as a degradation promoting agent and does not comprise a biodegradable polymer; and (c) a biodisintegrable exterior region, disposed between the interior region and an exterior environment of the device, which comprises a biodegradable polymer and a therapeutic agent, said solubilizing agent increasing the solubility of biodegradable polymer breakdown products from said exterior region, wherein said solubilizing agent is a polyoxyalkylene homopolymer, polyoxyalkylene copolymer, polyoxyalkylene ester, polyoxyalkylene ether, or combination thereof and wherein said device releases a single therapeutic agent.

28. The medical device of claim 27, wherein said solubilizing agent is a polyoxyalkylene sorbitan ester.

29. The medical device of claim 27, wherein said solubilizing agent is a polyethoxylated fatty acid ester of sorbitan.

30. The medical device of claim 27, wherein said solubilizing agent is a polysorbate.

31. The medical device of claim 27, wherein the interior region further comprises a particulate poragenic agent selected from potassium chloride, sodium chloride, calcium chloride and a sugar.

32. The medical device of claim 31, wherein said poragenic agent is a sugar.

33. The medical device of claim 27, wherein the interior region comprises 50 wt % or more of said degradation promoting agent.

34. The medical device of claim 27, wherein said biodisintegrable exterior region is disposed directly on said biodisintegrable interior region.

35. The medical device of claim 34, wherein the interior region further comprises a particulate poragenic agent.

36. The medical device of claim 35, wherein said poragenic agent is a sugar.

37. The medical device of claim 27, further comprising an organic acid.

* * * * *